United States Patent [19]
Long

[11] Patent Number: 5,193,672
[45] Date of Patent: Mar. 16, 1993

[54] SURGICAL INSTRUMENT CASE

[75] Inventor: Jack F. Long, Warsaw, Ind.

[73] Assignee: Depuy Inc., Warsaw, Ind.

[21] Appl. No.: 827,158

[22] Filed: Jan. 28, 1992

[51] Int. Cl.$^5$ ............... B65D 83/10; B65D 5/52; A61L 2/00; A61L 9/00

[52] U.S. Cl. .................. 206/45.2; 206/370; 422/300

[58] Field of Search ............ 206/363, 370, 369, 45.2; 433/77; 422/300

[56] References Cited

U.S. PATENT DOCUMENTS

| | | |
|---|---|---|
| 659,058 | 10/1900 | Edlen . |
| 682,522 | 9/1901 | Boekel ........................ 206/363 |
| 691,695 | 1/1902 | Aderer . |
| 805,583 | 11/1905 | Redlich ....................... 206/45.2 |
| 862,771 | 8/1907 | Taylor . |
| 1,684,417 | 9/1928 | Silberman .................... 206/369 |
| 1,905,556 | 4/1933 | Moore . |
| 2,523,877 | 9/1950 | Pestolesi . |
| 2,880,857 | 4/1959 | Parsons et al. ............. 206/45.2 X |
| 4,135,868 | 1/1979 | Schainholz . |
| 4,191,291 | 3/1980 | Brown . |
| 4,256,457 | 3/1981 | Behring . |
| 4,259,568 | 3/1981 | Dynesen ...................... 206/45.2 |
| 4,327,060 | 4/1982 | Nisii . |
| 4,448,307 | 5/1984 | Roggenkamp . |
| 4,573,569 | 3/1986 | Parker ........................ 206/45.2 |
| 4,589,551 | 5/1986 | Hellon ........................ 206/45.2 |
| 4,643,303 | 2/1987 | Arp et al. . |
| 4,762,688 | 8/1988 | Berry, Jr. . |
| 5,084,251 | 1/1992 | Thomas ........................ 422/300 |

Primary Examiner—William I. Price
Attorney, Agent, or Firm—Barnes & Thornburg

[57] ABSTRACT

A surgical instrument case suitable for autoclaving and instrument presenting to the surgeon during surgery comprising a container formed to include an interior region, cradle means for holding a variety of surgical instruments attached to the bottom of the container to be in the interior region; and a top. The top, when it is open, provides support means for propping the instrument case at an acute angle to the horizontal to provide easy access to the instruments by the surgeon while minimizing handling, the top being hingedly attached to the container. The cradle means is formed to include notches of various size to accommodate instruments of various sizes in laterally spaced-apart, upwardly extending positions when the instrument case is opened and propped up.

15 Claims, 2 Drawing Sheets

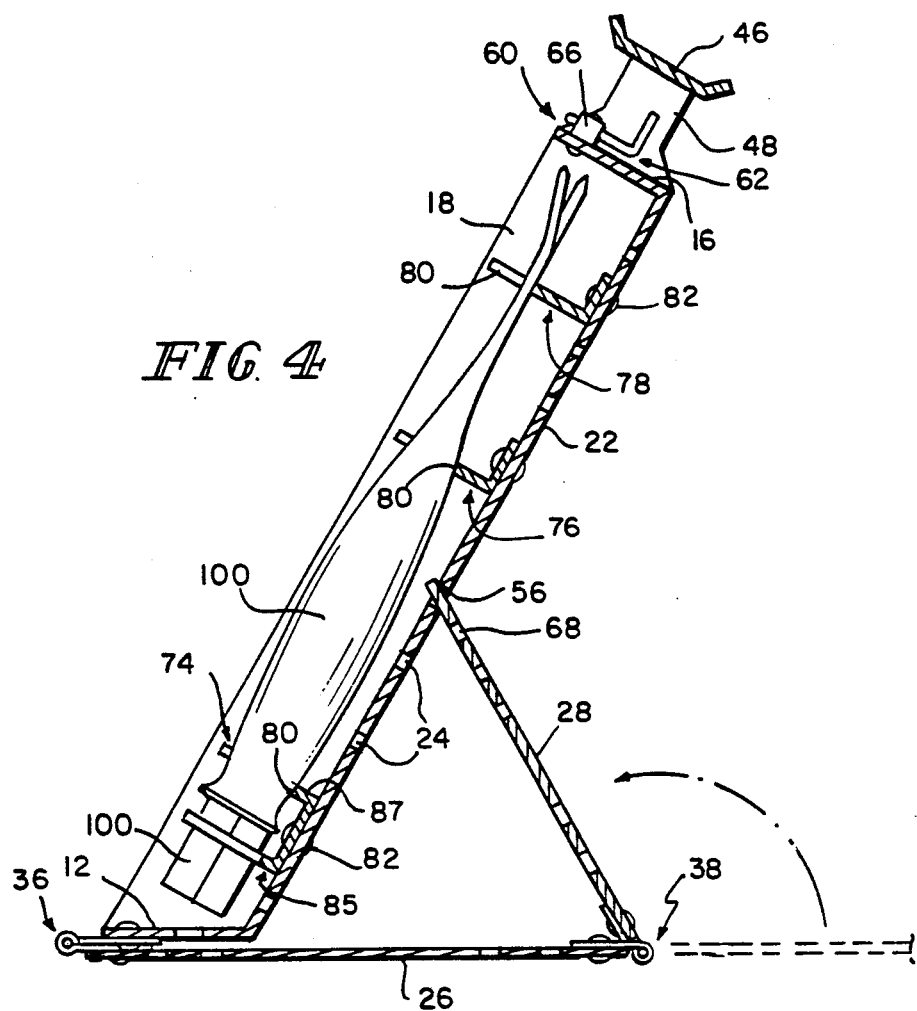
FIG. 4
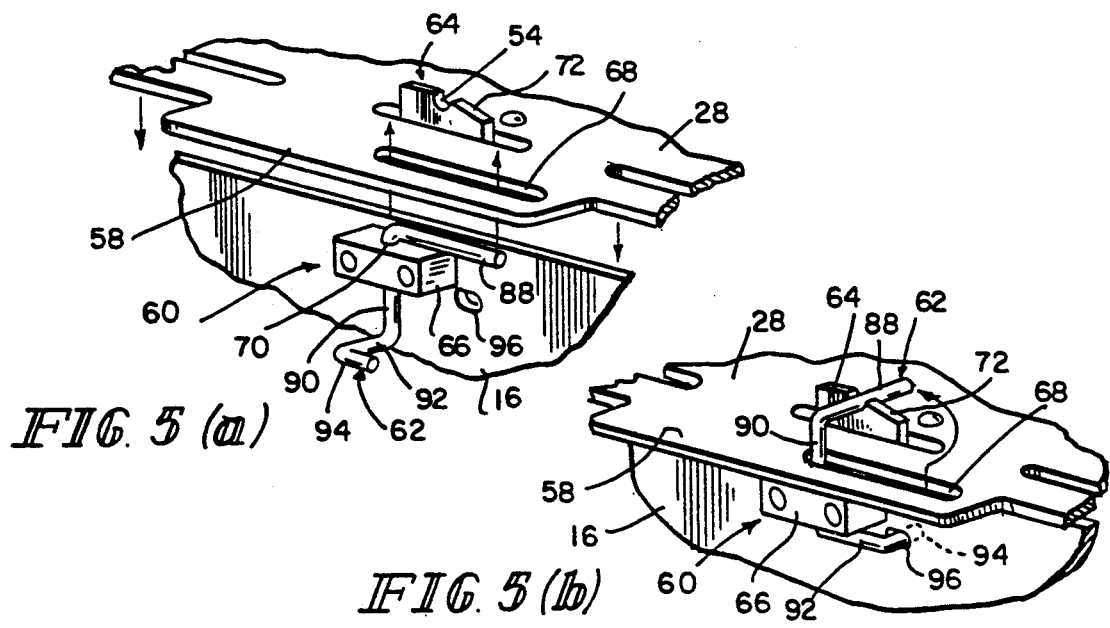
FIG. 5(a)
FIG. 5(b)

SURGICAL INSTRUMENT CASE

BACKGROUND AND SUMMARY OF THE INVENTION

The present invention relates to stackable surgical instrument cases suitable for autoclaving and particularly to stackable surgical instrument cases incorporating means for storing, transporting, and presenting of reusable surgical instruments to the surgeon during surgery.

A preliminary step to any surgical procedure is to have the surgical instruments and related components and accessories properly sterilized. This procedure involves subjecting the various parts and components to an autoclaving operation wherein these objects are subjected to an elevated temperature in the range of 270° F. and an elevated pressure.

One requirement for any autoclaving tray or instrument holder for these instruments and components is that it is able to withstand the elevated temperatures and pressure, and to do so for many cycles. Any tray or instrument holder which would become unsuitable for continued use after only a few autoclaving cycles represents a design deficiency, not only from the standpoint of cost but also from the standpoint of inventory control and the time and inconvenience associated with having to repeatedly replace a damaged or otherwise unsuitable autoclaving tray.

Surgical instrument cases and instrument cases for autoclaving are known in the prior art. See, for example, Schainholz, U.S. Pat. No. 4,135,868; Arp et al., U.S. Pat. No. 4,643,303; Moore, U.S. Pat. No. 1,905,556; Berry, Jr., U.S. Pat. No. 4,762,688; Nisii, U.S. Pat. No. 4,327,060.

In the past, after surgery, it has been the practice to co-mingle all of the instruments in a basket which is then placed within an autoclave and subjected to sterilizing steam. When ready for use, a surgical nurse would take the instruments from the autoclave basket and lay them out on a Mayo stand in a particular arrangement dictated by the surgeon so that they would be in convenient reach of the surgeon or the surgical nurse.

The co-mingling of the instruments in loose fashion in a basket and the transportation thereof has damaged them, rendering them unusable. There was no way to organize them and to protect them at the same time. This, of course, increases the time involved in the particular procedure.

In many instances, particularly in orthopaedic surgery, the surgical instruments used in the various procedures look very much alike and differ only in minor respects, such as size, angle of bend, tip type, etc. At a glance, it is difficult to discern one instrument from another and, therefore, the surgical nurse or operating surgeon may have a difficult time finding the right instrument to use at any given time. It is, of course, imperative that the surgeon be able to rapidly identify and select the appropriate instrument to be used at any given time without confusion and without any undue lapse of time.

The present invention is intended to overcome these problems in sterilizing, storing, transporting, and presenting reusable surgical instruments.

According to the present invention, a stackable surgical instrument case is provided that comprises a container perforated with apertures for the passage of fluid through the interior of the container, cradle means inside the container for holding a variety of surgical instruments, and a top, which is hingedly attached to the container. The top, when the case is open, provides support for propping the instrument case at an acute angle to the horizontal to provide easy access to the instruments by the surgeon while minimizing handling. One aspect of the present invention includes cradles which are formed to include notches of various size to accommodate instruments of various sizes in laterally spaced-apart, upwardly extending positions when the instrument case is opened and propped up. Another aspect of the invention includes a handle attached to the container for facilitating handling of the instrument case. The handle comprises three portions. Two of the portions are attached to, and form extensions of, two opposing side walls, and a third portion connects the side wall extensions across a third side wall.

According to another aspect of the invention, the top comprises two sections and two hinges. The first hinge connects the proximal edge of the first portion of the top to a side wall for hinge movement about an axis, and the second hinge attaches the distal edge of the first portion to the proximal edge of the second portion of the top. Means for engaging the bottom of the container are formed along the distal edge of the second top portion. The support means is formed by rotating the first top portion about the first hinge so that the first top portion lies parallel to the first side wall. By rotating the second top portion about the second hinge, the engaging means on the distal edge of the second top portion can engage the bottom. According to yet another aspect of the invention, the first side wall is formed at an angle to the horizontal equal to the angle formed by the supporting means.

In another illustrative embodiment of the present invention, the case comprises a container having rectangularly arranged walls, a top and a bottom formed to include apertures, and a handle attached to the container. The walls have a height sufficient to accommodate the instruments. The top provides the support means for propping the case at an acute angle to the horizontal. A surgical instrument cradle is attached to the bottom of the inside of the container, and the cradle is formed to include notches. The top is formed to include a first top portion and a second top portion and a locking tab on the second top portion. It further includes a first hinge means for connecting the first top portion to the case and a second parallel hinge means for connecting the second top portion to the first top portion. A first wall is formed at an angle to the bottom wherein the angle formed is the supplement of the angle formed by the support means. According to one aspect of the invention, the handle is of the same height as the walls.

Additional objects, features, and advantages of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 4 is a sectional view of the instrument case in a presenting position showing the top arranged to support the case;

FIG. 5(a) is a detailed view of the closure mechanism in the non-engaged position; and FIG. 5(b) is a detailed view of the closure mechanism in the engaged position.

DETAILED DESCRIPTION OF THE DRAWINGS

Figure 1:
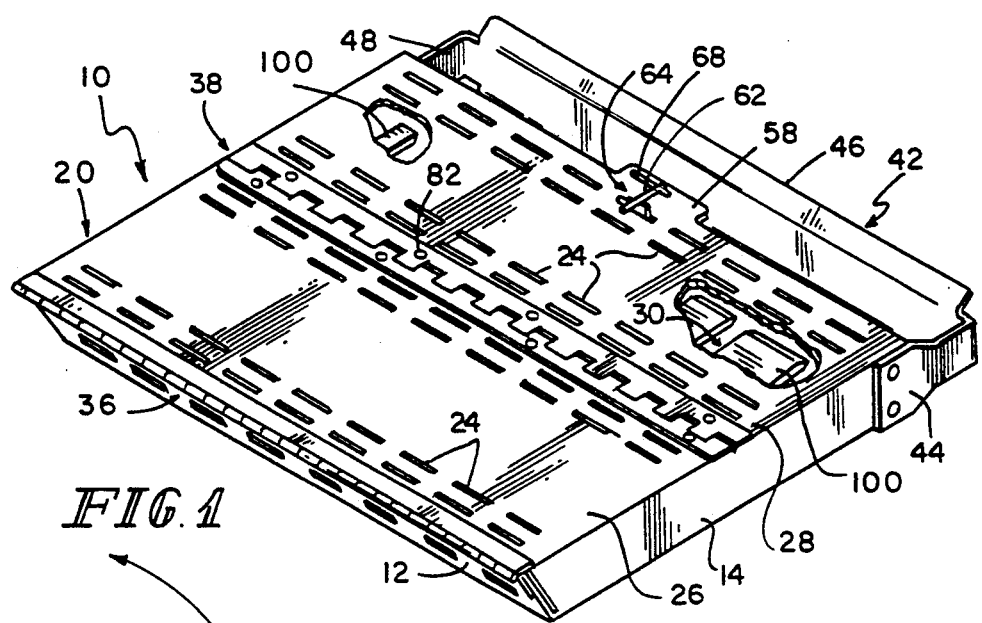
FIG. 1 is a perspective view of the surgical instrument case with portions broken away revealing instruments arranged in the interior.

A stackable surgical instrument case suitable for autoclaving which facilitates the sterilizing, storing, protecting, handling, and presenting during surgery of a variety of surgical instruments and devices is shown generally at 10. The case 10 comprises a first side wall, second side wall, third side wall, and fourth side wall 12, 14, 16, and 18 respectively, a top 20 and a bottom 22. The side walls 12, 14, 16, 18 are of sufficient height to accommodate instruments. In the illustrative embodiment, the top 20, the bottom 22 and the first side wall 12 are perforated with apertures 24. The illustrative apertures 24 provide passage for steam or hot water through the interior region during autoclaving. The general construction of the instrument case and cradles is of stainless steel in order to provide durability through repeated cycles of elevated temperature and pressure during autoclaving between surgical use. The illustrative attachments are generally in the form of rivets 82. However, other suitable materials may be used for the construction, and other fastening means such as welding, can be used. The apertures that facilitate autoclaving may take different shapes and forms, and the walls may include apertures to accommodate autoclaving.

The top 20 comprises a first portion 26 and a second portion 28. A first hinge 36 attaches a proximal edge of the first portion 26 to a top edge of the first side wall 12. The second hinge 38, parallel to the first hinge 36, attaches a distal edge of the first portion 26 to a proximal edge of the second portion 28. The lower edge of the first wall 12 is attached to the bottom 22 at an obtuse angle.

Figure 2:
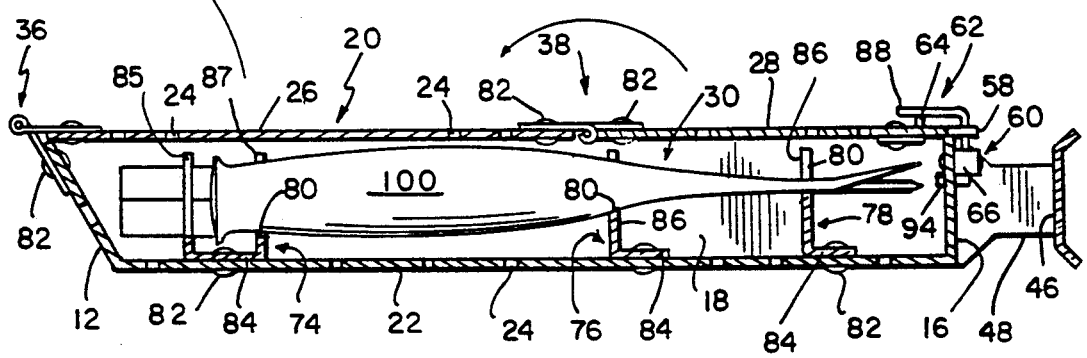
FIG. 2 is a sectional view taken through the instrument case revealing instruments resting in cradles inside the instrument case.
Figure 3:
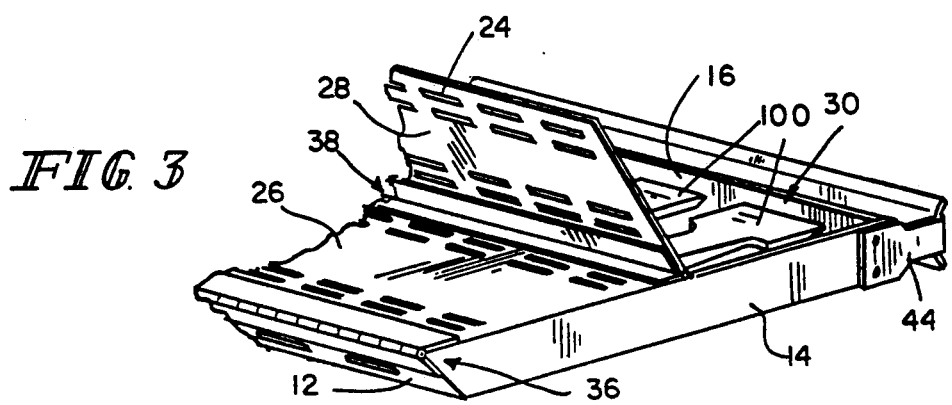
FIG. 3 is a fragmentary perspective view of a portion of the surgical instrument case with the top partially opened.

A handle 42 is attached to the case 10 opposite the first wall 12. The handle 42 comprises a first portion, a second portion and a third portion, 44, 46, and 48 respectively. The first portion 44 is attached to, and forms an extension of the second side wall 14. The second portion 46 extends generally perpendicularly from the first portion 44 and parallel to and spaced apart from the third side wall 16. The third handle portion 48 extends generally perpendicularly from the second handle portion 46 and parallel to the first handle portion 44. The third portion 48 attaches to, and forms an extension of, the fourth side wall 18. As best seen in FIG. 2, the handle 42 is designed to be no higher than the side walls 14, 16, and 18 in order to ensure stackability inside the autoclave.

The top 20, when the instrument case 10 is open, forms a support means for propping up the case 10 at an acute angle to the horizontal, as shown in FIG. 4, providing ready access to the instruments as well as complete visual inspection by the surgeon, while minimizing handling of the instruments between autoclaving and surgery. To engage the support mechanism, the first top portion 26 is rotated about the first hinge 36 to lie parallel to the first side wall 12, as best shown in FIG. 4. The second top portion 28 is rotated about the second hinge 38 toward the bottom 22. An engaging means, such as the illustrative tabular extension 58 formed along the distal edge of the second top portion 28, is inserted into an engaging aperture 56 formed in the bottom 22 of the instrument case 10. The tabular extension 58 is wider than the apertures 24 formed in the container. The illustrative engaging aperture 56 is a particular aperture made wide enough to engage the tabular extension 58, and is aligned with the tabular extension 58. As the instrument case 10 is rotated from near vertical toward the horizontal the tabular extension 58 slides along the bottom 22 toward the engaging aperture 56. Because of the sizing and alignment of the tabular extension 58 and aperture 56, the tabular extension 58 automatically slides into and engages the engaging aperture 56. This allows quick and easy set up of the instrument case 10 in a position for presentment of the instruments to the surgeon. At the same time, the triangle formed by the first top portion 26, the second top portion 28, and the bottom 22 forms a stable support for the instrument case 10 during surgery.

Instrument cradles 74, 76, 78 hold the instruments in position within the instrument case 10, as best seen in FIGS. 2 and 4. A handle cradle 74, a shank cradle 76 and a blade cradle 78 are attached to the bottom 22 and extend upwardly into the interior region 30 and hold the instruments 100 in a laterally spaced-apart, upwardly extending positions for presentment to the surgeon. The shank cradle 76 and the blade cradle 78 each have a base portion 84 and a vertical portion 86 formed at right angles to each other. The base portion 84 lies adjacent to the bottom 22 and is attached thereto by rivets 82. The vertical portion 86 extends perpendicularly from the base portion 84 into the interior region 30 of the case 10. The handle cradle 74 is formed of three portions, a base portion 84 being adjacent to the bottom 22 and attached thereto by rivets and a first and second vertical portions 85, 87. The vertical portions 85, 87 extend perpendicularly from the base portion 84 upwardly into the interior region 30 of the case 10. The cradles 74, 76, 78 extend laterally between the second side wall 14 and the fourth side wall 18 in a parallel spaced-apart relation to each other. The cradles 74, 76, 78 are of sufficient height to prevent the instruments 100 from falling out of the notches 80 while the case is closed for autoclaving or transport.

The cradles 74, 76, 78 have a series of notches 80 cut into them. The notches in the blade cradle 78 are rectangular in shape and of equal depth. The width of the blade notches 78 varies in order to accommodate instruments 100 with blades of various widths. The separation between notches decreases as the width of the blade of the surgical instruments 100 increases from left to right as viewed by the surgeon. The notches in the shank cradle 76 are U-shaped and of equal size. The distance between each notch increases from left to right as viewed by the surgeon. This is necessary in order to accommodate blades of increasing width. The handle cradle 74 has notches in each of the vertical portions 85, 87 of the cradle 74. The notches in the first vertical portion 85, the portion closest to the first wall 12, are all rectangular and of the same depth. The notches in the second vertical portion 87 of the handle cradle 74 are U-shaped and of equal width and depth. As with the notches in the shank cradle 76, the notches in the handle cradle 74 are spaced increasingly farther apart from left to right. The notches in the three cradles 74, 76, 78 are aligned such that the instruments are displayed in a laterally spaced-apart, upwardly extending, parallel position. In addition, apertures 24 formed in the first side wall 12 are aligned with the notches 80 to act as additional support means for instruments 100 with particularly long and/or narrow handles.

After use, the instruments 100 are arranged in the instrument case 10 and prepared for autoclaving. The tabular extension 58 is removed from the engaging aperture 56, and the top is rotated about the hinges back to its closed position as shown in FIG. 1.

A closure means 60 (FIGS. 5(a) and (b)) is provided to maintain the instrument case 10 in a closed position. The illustrative closure means comprises a latch 62, a latching tab 64, a holding block 66 and a latch slot 68 in portion 28 of the top. The illustrative latch 62 is a stainless steel dowel formed into four portions 88, 90, 92, and 94 respectively. The second latch portion 90 is formed perpendicularly to the first portion 88. The third latch portion 92 is formed perpendicularly to both the first latch portion 88 and the second portion 90. The fourth latch portion 94 is formed to be perpendicular to both the second latch portion 90 and the third latch portion 92, and to be parallel to the first latch portion 88. The illustrative holding block 66 is mounted to the third side wall 16 by rivets, welding or other means. A "groove" or "bore" 70 is cut into the holding block 66 slidably and rotatably to engage the second latch portion 90, thereby coupling the latch 62 to the instrument case 10. The latching tab 64 is attached to the second top portion 28 and extends upwardly away from the interior region 30 of the instrument case 10. The latch slot 68 is formed in the tabular extension 58, whereby the latch slot 68 is sized and aligned to receive the first latch portion 88, which passes therethrough and rotates 90° to engage the latching tab 64. A beveled or inclined surface 72 is formed on the latching tab 64 to allow easy engagement of the first latch portion 88 with the latching tab 64. The latch tab 64 has a notch 54 for engaging the latch portion 88, and the movement of the latch portion 88 up the incline 72 stresses the latch portion to provide resistance to its movement away from the locked position. A latch aperture 96 is formed in the third side wall 16 in a position to receive the fourth latch portion 94 when the first latch portion 88 has engaged the latching tab 64. It is the combination of the fourth latch portion 94 inside the latch aperture 96 and the first latch portion 88 engaging the latching tab 64 that prevents the top 20 from opening. While the illustrative locking means or closure means 60 works well, it will be appreciated that a number of different types of locks may be used releasably to hold the case 10 closed.

Although the invention has been described in detail with reference to certain preferred embodiments, variations and modifications exist within the scope and spirit of the invention as described and defined in the following claims.

I claim:

1. A surgical instrument case suitable for autoclaving and instrument presenting to the surgeon during surgery, the case comprising:
   a container formed to include an interior region defined by a plurality of side walls, top and bottom, at least said top and bottom being perforated with apertures for passage of fluid through said interior region during autoclaving;
   one of said side wall acutely angled with respect to the top wall to define an inclination angle for the surgical case;
   cradle means for holding a variety of surgical instruments, said cradle means being attached to the bottom to be in said interior region; and
   said top hingedly attached to said one acutely angle side wall for pivoting from its acute angle when closed to overlie and be in parallelism with the one said acutely angled wall, when it is open, for providing support for propping the instrument case at the acute inclination angle to the horizontal to provide easy access to the instruments by the surgeon while minimizing handling.

2. The case of claim 1, wherein the cradle means is formed to include notches of various size to accommodate instruments of various sizes in laterally spaced-apart, upwardly extending positions when said instrument case is opened and propped up.

3. The case of claim 1, further comprising handle means attached to the container for facilitating handling of the instrument case, said handle means having three portions, a first portion being attached to a side wall and forming an extension thereof, a second portion extending perpendicularly to the first portion and in a spaced-apart relation to another side wall, and a third portion extending perpendicularly to the second portion, the third portion being attached to, and forming an extension of, yet another side wall.

4. The case of claim 1, in which said top comprises a first top portion and a second top portion, said first top portion being hingedly connected by a first hinge at its proximal edge to a first side wall for hinge movement about an axis, said first top portion having a distal edge parallel to its proximal edge, said second top portion being hingedly connected by a second hinge at its proximal edge to the distal edge of said first top portion, said second top portion having means for engaging said bottom on its distal edge.

5. The case of claim 4, wherein the support function is obtained by rotating the first top portion about the first hinge so that the first top portion lies parallel to the first side wall and by rotating the second top portion of the top about the second hinge so that the engaging means on the distal edge of the second top portion can engage the bottom.

6. The case of claim 4, wherein the first side wall hingedly attached to the top is attached to the bottom and is formed at an obtuse angle to the bottom, the obtuse angle being approximately the supplement of the acute angle formed by the support means.

7. A relatively shallow, stackable surgical instrument case suitable for autoclaving and instrument presenting to the surgeon during surgery, the case comprising:
   rectangularly arranged walls, a top and a bottom providing a container having an interior region, at least with said top and bottom formed to include apertures, said walls having a height sufficient to accommodate instruments;
   said top providing support means for propping the case at an acute angle to the horizontal;
   a surgical instrument cradle attached to the bottom to be inside the interior region, wherein the cradle is formed to include notches;
   the top formed to include a first top portion and a second top portion, first hinge means for connecting said first top portion to said case and second parallel hinge means for connecting said second top portion to said first top portion, and a locking tab on said second top portion; and a first wall formed at an angle to the bottom wherein the angle formed is the supplement of the angle formed by the support means.

8. The case of claim 7, wherein a first hinge means connects the first top portion to a first wall, and said second hinge connects the second top portion to the first top portion.

9. The case of claim 8, wherein the support means is formed by rotating the first top portion about the first hinge to lie parallel to the first wall, and rotating the second top portion about the second hinge to enable the locking tab to engage the bottom.

10. The case of claim 7, wherein the notches are of various sizes to accommodate instruments of various sizes.

11. The case of claim 7 wherein the case includes a handle.

12. A surgical instrument case suitable for autoclaving and instrument presenting to the surgeon during surgery, the case comprising:

a container formed to include an interior region defined by a plurality of side walls, top and bottom, at least said top and bottom being perforated with apertures for passage of fluid through said interior region during autoclaving cradle means for holding a variety of surgical instruments, said cradle means being attached to the bottom to be in said interior region;

said top, when it is open, providing support means for propping the instrument case at an acute angle to the horizontal to provide easy access to the instruments by the surgeon while minimizing handling, said top being hingedly attached to said container;

wherein said top comprises a first top portion and a second top portion, said first top portion being hingedly connected by a first hinge at its proximal edge to a first side wall for hinge movement about an axis, said first top portion having a distal edge parallel to its proximal edge, said second top portion being hingedly connected by a second hinge at its proximal edge to the distal edge of said first top portion, said second top portion having means for engaging said bottom on its distal edge; and wherein the support means is formed by rotating the first top portion about the first hinge so that the first top portion lies parallel to the first side wall to provide a support surface for the support means and by rotating the second top portion of the top about the second hinge so that the engaging means on the distal edge of the second top portion can engage the bottom.

13. The case of claim 12, wherein the first side wall hingedly attached to the top is attached to the bottom and is formed at an obtuse angle to the bottom, the obtuse angle being approximately the supplement of the acute angle formed by the support means.

14. A relatively shallow, stackable surgical instrument case suitable for autoclaving and instrument presenting to the surgeon during surgery, the case comprising:

rectangularly arranged walls, a top and a bottom providing a container having an interior region, at least with said top and bottom formed to include apertures, said walls having a height sufficient to accommodate instruments;

said top providing support means for propping the case at an acute angle to the horizontal;

a surgical instrument cradle attached to the bottom to be inside the interior region;

the top formed to include a first top portion and a second top portion, first hinge means for connecting said first top portion to one of said rectangular arranged walls and second parallel hinge means for connecting said second top portion to said first top portion;

said first top portion being pivotal about said first hinge means to provide a support surface for the support means; and said one rectangular wall formed at an angle to the bottom wherein the angle formed is the supplement of the angle formed by the support means.

15. A surgical instrument case suitable for autoclaving and instrument presenting to the surgeon during surgery, the case comprising:

a container formed to include an interior region defined by a plurality of side walls, top and bottom, at least said top and bottom being perforated with apertures for passage of fluid through said interior region during autoclaving;

cradle means for holding a variety of surgical instruments, said cradle means being attached to the bottom to be in said interior region;

said top, when it is open, providing support means for propping the instrument case at an acute angle to the horizontal to provide easy access to the instruments by the surgeon while minimizing handling, said top being hingedly attached to said container;

wherein said top comprises a first top portion and a second top portion, said first top portion being hingedly connected by a first hinge at its proximal edge to a first side wall for hinge movement about an axis, said first top portion having a distal edge parallel to its proximal edge, said second top portion being hingedly connected by a second hinge at its proximal edge to the distal edge of said first top portion, said second top portion having means for engaging said bottom on its distal edge; and wherein the first side wall hingedly attached to the top is attached to the bottom and is formed at an obtuse angle to the bottom, the obtuse angle being approximately the supplement of the acute angle formed by the support means.

* * * * *